United States Patent [19]

Scholz

[11] 4,429,048

[45] Jan. 31, 1984

[54] ALIPHATIC AMINE-CONTAINING KARL FISCHER TITRATION AGENT AND METHOD FOR USING IT

[75] Inventor: Eugen Scholz, Garbsen, Fed. Rep. of Germany

[73] Assignee: Riedel-de Haen Ag., Seelze, Fed. Rep. of Germany

[21] Appl. No.: 412,214

[22] Filed: Aug. 27, 1982

Related U.S. Application Data

[62] Division of Ser. No. 210,857, Nov. 26, 1980, Pat. No. 4,378,972.

[30] Foreign Application Priority Data

Mar. 5, 1980 [DE] Fed. Rep. of Germany ....... 3008421
Oct. 20, 1980 [DE] Fed. Rep. of Germany ....... 3039511

[51] Int. Cl.³ .......................................... G01N 33/18
[52] U.S. Cl. ........................................ 436/42; 73/73; 116/26
[58] Field of Search ...................... 252/408; 23/230 R; 436/42; 73/73; 116/206

[56] References Cited

U.S. PATENT DOCUMENTS

| | | | |
|---|---|---|---|
| 2,967,155 | 1/1961 | Blomgren et al. | 252/408 |
| 3,656,907 | 2/1970 | Delmonte . | |
| 3,661,797 | 6/1970 | Meloan . | |
| 3,974,258 | 8/1976 | Poitevin et al. | 423/242 |
| 4,005,983 | 6/1974 | Dahms . | |
| 4,146,454 | 3/1979 | Haber | 204/180 G |
| 4,378,972 | 4/1983 | Scholz | 436/42 |
| 4,385,124 | 5/1983 | Verbeek et al. | 436/42 |

OTHER PUBLICATIONS

Analytical Chemistry vol. 28, No. 7, 1166–1168 (1956).
J. Am. Chem. Soc. vol. 61, 2407–2412 (1939).
Analytica Chimica Acta vol. 94, 395–403 (1977).
American Laboratory, Vol. 13, No. 8, pp. 89–91, "Pyridine-free Karl Fischer Reagents."

*Primary Examiner*—Benjamin R. Padgett
*Assistant Examiner*—M. Moskowitz
*Attorney, Agent, or Firm*—Curtis, Morris & Safford

[57] ABSTRACT

For the titrimetric determination of small amounts of water, the Karl Fischer reagent is used which contains sulfur dioxide, iodine and pyridine as essential components. Replacement of pyridine by specific nitrogen bases is advantageous. Particularly suitable are selected aliphatic amines and nitrogen-containing heterocyclic compounds, especially imidazoles. The pyridine-free titration agent is distinguished by high storage stability; it can be used as bicomponent or monocomponent reagent.

14 Claims, 1 Drawing Figure

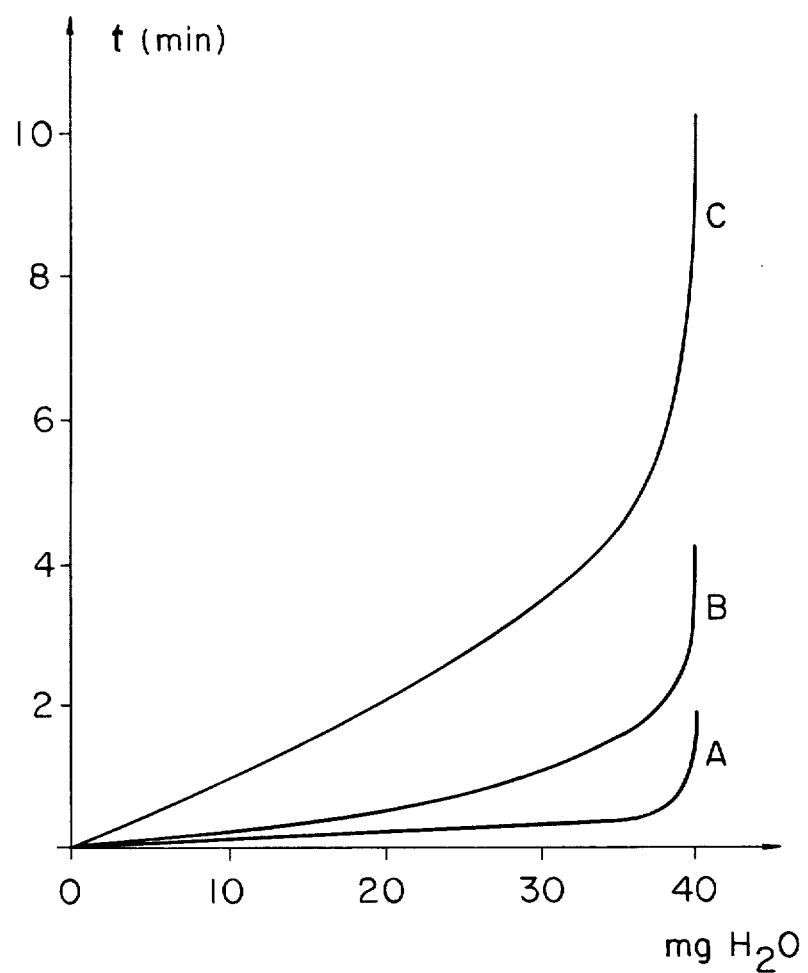

ALIPHATIC AMINE-CONTAINING KARL FISCHER TITRATION AGENT AND METHOD FOR USING IT

This is a division of application Ser. No. 210,857 filed 11/26/80, now U.S. Pat. No. 4,378,972, issued Apr. 12, 1983.

The invention provides a titration agent containing an amine, sulfur dioxide and iodine, and a method for using same for determining the water content of solid substances or liquids.

As is known, titrimetric determination of the water content in liquids and solids was developed by Karl Fischer. This method is based on the oxidation of sulfur dioxide by iodine in the presence of water according to the following scheme:

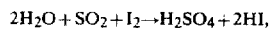

$2H_2O + SO_2 + I_2 \rightarrow H_2SO_4 + 2HI$,

Usually, the reaction is carried out in anhydrous methanol; the reagent consisting of a solution of 790 g of pyridine, 192 g of liquid sulfur dioxide and 254 g of iodine in 5 liters of anhydrous methanol (see Angew. Chemie Vol. 48 (1935), 394). Since this solution is not stable on storage, a bicomponent reagent is generally used in the practice, which consists of a solution of sulfur dioxide and pyridine in methanol on the one hand, and on the other of a solution of iodine in methanol.

It is furthermore known that other nitrogen bases were used instead of pyridine, for example quinoline, aniline, dimethylaniline, tri-n-butylamine and triethanolamine (see J. Amer. Chem. Soc. 1939, 2407), but did not bring about satisfactory results. Further amines intended for replacing the pyridine are ethanolamine and hexamethylene-tetramine; however, these amines are said to have the disadvantage of showing no stable titration point or causing troublesome precipitations (see Analytic. Chem. Vol. 28 (1956), 1166). The KF reagent so modified served for determining the water content in oxidants, reducing agents and amines.

It is the object of the invention to provide a reagent suitable for determining small amounts of water, which instead of pyridine contains a substantially nontoxic amine, and is stable on storage.

The invention provides a titration agent containing an amine, sulfur dioxide and iodine, wherein the amine is (a) an aliphatic amine optionally containing 1, 2 or 3 oxygen atoms, the molar ratio of amine to sulfur dioxide being from 0.5:1 to 1.3:1; or (b) a five- or six-membered, optionally substituted, heterocyclic compound having at least 2 hetero-atoms, 1 hetero-atom at least being a nitrogen atom.

As amine base, the titration agent of the invention contains (a) an aliphatic amine which is cyclic or, preferably, acyclic. It may have 1, 2 or 3 oxygen atoms, preferably in the form of hydroxy groups. Especially suitable is an acyclic primary amine having from 2 to 6 carbon atoms and optionally 1, 2 or 3 hydroxy groups. Suitable amines are for example: morpholine, piperidine, piperazine, n-propylamine, isopropylamine, diethylamine, triethylamine, dimethylamino-propylamine, ethanolamine, diethanolamine, triethanolamine, tris(hydroxymethyl)-aminomethane or guanidine. The molar ratio of amine to sulfur dioxide is preferably in the range of from 0.8:1 to 1.2:1.

The heterocyclic compound contained as amine base (b) in the titration agent has five or six ring members and is optionally substituted, preferably by 1, 2 or 3 alkyl radicals having from 1 to 4 carbon atoms, or by 1, 2 or 3 phenyl radicals or a benzo group; the heterocyclic compound contains at least 2, preferably 2 or 3, hetero-atoms, one of which at least is a nitrogen atom. Especially suitable is a five-membered, optionally substituted, heterocyclic compound having 2 nitrogen atoms as hetero-atoms. The molar ratio of heterocyclic compound to sulfur dioxide is generally in the range of from 10:1 to 0.3:1, preferably 2:1 to 0.5:1.

As heterocyclic compound, imidazole or a derivative thereof is especially suitable; preferred, however, is a compound of the formula

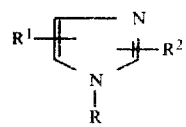

in which R, $R^1$ and $R^2$, being identical or different, each represent a hydrogen atom, a lower alkyl radical having preferably from 1 to 4 carbon atoms, or a phenyl radical.

Examples of heterocyclic compounds to be used in accordance with the invention are above all: imidazole, 1-methylimidazole, 1-ethylimidazole, 1-propylimidazole, 1-butylimidazole, 2-methylimidazole, 2-ethylimidazole, 2-propylimidazole, 2-butylimidazole, 4-methylimidazole, 4-butylimidazole, 1,2-dimethylimidazole, 1,2,4-trimethylimidazole, 1-phenylimidazole, 2-phenylimidazole and benzimidazole, furthermore imidazoline, 2-methylimidazoline (lysidine), 2-phenylimidazoline, and thiazole, 2-methylthiazole, 2-ethylthiazole, 4-methylthiazole, 4-ethylthiazole, 2-phenylthiazole, 4-phenylthiazole, benzothiazole, pyrimidine, 4-methylpyrimidine, 4-ethylpyrimidine, 1,3,5-triazine and 1,2,4-triazine.

As solvent for the reactants of the titration agent of the invention, an anhydrous low molecular weight alcohol is used, preferably methanol or ethyleneglycol monomethyl ether, in an amount of from 2 to 50, preferably 5 to 20, mols (relative to 1 mol of amine).

The sulfur dioxide may alternatively be used in admixture with an acid, preferably a carboxylic acid; the molar ratio of sulfur dioxide to acid being from 20:1 to 1:5, preferably 2:1 to 1:2. Suitable acids are for example formic, oxalic, sulfuric, hydriodic, and especially acetic acid.

The titration agent of the invention is prepared by dissolving the amine, the sulfur dioxide and the iodine in the alcohol, optionally with cooling to a temperature of from 15° to 50° C., preferably 20° to 40° C. The amount of amine is from 0.1 to 10, preferably 0.5 to 5, mols, that of sulfur dioxide from 0.1 to 10, preferably 0.5 to 3, mols, and that of iodine from 0.01 to 3, preferably 0.1 to 1, mol (each relative to 1 liter of solution). The solution is prepared according to known methods with exclusion of atmospheric moisture and with the use of purified starting materials.

The titration agent of the invention is especially suitable for determining small amounts of water according to the Karl Fischer method. Thus, the invention provides furthermore a method for quantitative determination of small amounts of water by means of a reagent containing an amine, sulfur dioxide and iodine, which comprises using the titration agent of the invention as reagent.

By means of the titration agent of the invention, the water content of solid or liquid substances is determined, for example that of inorganic salts, organic solvents, fats, oils, food, or pharmaceutical products.

The titration agent of the invention is distinguished by a high stability on storage. It is suitable for use as bicomponent reagent as well as monocomponent reagent. In the form of bicomponent reagent, its storage stability is at least 12 months, and at least 2 years when using the amine base (b). In the form of the monocomponent reagent, it is stable for about 3 weeks, and about 1 year when using the amine base (b). A special advantage of the titration agent of the invention resides in the fact that it allows a high reaction speed (see Examples of application). Furthermore, the titration agent is distinguished in that the end point of titration is visually well recognizable by the change in color from colorless to brown. When using the agent in commercial automatic titration equipment with voltametric indication or dead-stop indication, very stable end points are obtained, thus ensuring high precision of the resulting water content data. The titration agent is furthermore suitable for use as electrolyte in the coulometric water content determination.

The following examples illustrate the invention.

The accompanying FIGURE illustrates titration curves obtained in accordance with titration examples of the application.

The course of the titration according to the Examples of application (b), (c) and (d) is recorded by a commercial automatic titration apparatus. The accompanying drawing shows the curves obtained: curve A = titration according to Example of application (b), curve B = titration according to Example of application (c), and curve C = titration according to Example of application (d) (Comparative Example).

EXAMPLE 1

(a) 420 ml of methanol are mixed with 250 g (2.87 mols) of morpholine, and 190 g (2.97 mols) of sulfur dioxide are introduced into the mixture with cooling to a temperature of 35° to 40° C. (solution A). The molar ratio of amine to $SO_2$ is 0.97:1.

(b) 85 g (0.67 mol) of iodine are dissolved in 1 liter of methanol (solution B).

(c) The solutions A + B form a bicomponent reagent. Solution A is added to the test solution, and titration is carried out with solution B.

EXAMPLE 2

(a) 56 g (0.87 mol) of sulfur dioxide are first introduced into 500 mol of methanol with cooling to 50° C., and 61 g (0.50 mol) of tris-(hydroxymethyl)aminomethane are then added to the mixture (solution A). The molar ratio of amine to $SO_2$ is 0.57:1.

(b) Solution B is identical with solution B of Example 1.

EXAMPLE 3

(a) 96 g (1.50 mols) of liquid sulfur dioxide are added to a solution of 100 g (1.69 mol) of n-propylamine in 600 ml of methanol, the temperature of the mixture being maintained by cooling at 35° to 40° C. (solution A). The molar ratio of amine to $SO_2$ is 1.12:1.

(b) Solution B is identical with solution B of Example 1.

EXAMPLE 4

(a) 157 g (1.49 mols) of diethanolamine, 60 g (1.0 mol) of acetic acid and 49 g (0.77 mol) of liquid sulfur dioxide are added one after the other to 800 ml of methanol, the temperature of the mixture being maintained by cooling at 30° to 35° C. (solution A). The molar ratio of amine to $SO_2$ is 0.84:1.

(b) Solution B is identical with solution B of Example 1.

EXAMPLE 5

A solution of 85 g (0.67 mol) of iodine in 1 liter of methanol is mixed with a solution of 157 g (1.49 mols) of diethanolamine, 60 g (1.0 mol) of acetic acid and 49 g (0.77 mol) of liquid sulfur dioxide in 800 ml of methanol. The molar ratio of amine to $SO_2$ is 0.84:1. The monocomponent reagent obtained can be used for 30 days.

EXAMPLE 6

157 g (1.49 mols) of diethanolamine, 92 g (1.43 mols) of liquid sulfur dioxide and 85 g (0.67 mol) of iodine are added one after the other to 820 ml of ethyleneglycol monomethyl ether; the temperature of the mixture being maintained by cooling at 30° C. The molar ratio of amine to $SO_2$ is 1.03:1. The monocomponent reagent obtained can be used for 1 year.

EXAMPLE 7

(a) 200 g of 2-aminothiazole (2 mols) are dissolved in 550 ml of methanol. Subsequently, with constant cooling to 15° to 20° C., 130 g of gaseous sulfur dioxide (2.03 mols) are introduced (solution A). The molar ratio of thiazole to $SO_2$ is 0.98:1.

(b) 85 g (0.67 mol) of iodine are dissolved in 1 liter of methanol (solution B).

(c) The solutions A + B form a bicomponent reagent. Solution A is added to the test solution, while solution B serves for titration.

EXAMPLE 8

(a) 120 g (1.86 mols) of sulfur dioxide are first introduced into 700 ml of methanol with cooling to a temperature of 20° C. Subsequently, 300 g (3.65 mols) of 2-methyl-imidazole are added with agitation and cooling in such a slow manner that the temperature does not exceed 30° C. The molar ratio of imidazole to $SO_2$ is 1.96:1.

(b) Solution B is identical with solution B of Example 7.

EXAMPLE 9

204 g (3 mols) of imidazole are dissolved in 700 g of ethyleneglycol-monomethyl ether. Subsequently, 128 g (2 mols) of sulfur dioxide are introduced, while the temperature is maintained with cooling at 25° to 30° C. Thereafter, 100 g (0.8 mol) of iodine are added. The monocomponent reagent so obtained can be used for 1 year.

EXAMPLES OF APPLICATION (a) 20 ml of methanol containing 40 mg of water is titrated with the titration agent obtained according to Example 3 in a commercial automatic titration apparatus. The titration is terminated after 140 seconds.

(b) 20 ml of methanol containing 40 mg of water is titrated with the titration agent obtained according to Example 8. Titration is terminated after 80 seconds (see curve A of the accompanying drawing). The end point of the titration can also be determined visually, because it is indicated by a color change of colorless to brown.

(c) 40 mg of water are titrated with a solution according to Example 9 in a titration apparatus. Titration is terminated after 190 seconds, and attains exactly the value of 40 mg of water, which indication remains unchanged for a further 10 minutes (see curve B).

(d) Test (a) is repeated with a known KF reagent which, per liter of ethyleneglycol-monomethyl ether, contains 250 g (3.16 mols) of pyridine, 90 g (1.40 mols) of sulfur dioxide and 140 g (1.10 mols) of iodine. Titration is possible only with the use of a commercial automatic titration apparatus, because it does not show any satisfactory change in color at the equivalent point. Titration time is 545 seconds (see curve C); the end point does not remain constant.

(e) Test (a) is repeated with a known KF reagent which per liter of methanol contains 700 g (8.85 mols) of pyridine, 81 g (1.27 mols) of sulfur dioxide and 130 g (1.02 mols) of iodine, and which has a molar ratio of amine to $SO_2$ of 7:1. Titration time is 350 seconds.

What is claimed is:

1. A titration agent consisting essentially of an amine, sulfur dioxide and iodine, wherein the amine is an acyclic primary amine having from 2 to 6 carbon atoms and the molar ratio of amine to sulfur dioxide is from 0.5:1 to 1.3:1.

2. The titration agent of claim 1, wherein the amine is an acyclic primary amine having from 2 to 6 carbon atoms and containing 1, 2 or 3 hydroxy groups.

3. The titration agent of claim 1, further including an anhydrous low-molecular weight alcohol.

4. A titration agent consisting of an acyclic primary amine having from 2 to 6 carbon atoms, sulfur dioxide, iodine and an anhydrous low-molecular weight alcohol, the molar ratio of amine to sulfur dioxide being from 0.5:1 to 1.3:1.

5. The titration agent of claim 4, wherein the alcohol is present in an amount of from 2 to 50 mols, relative to 1 mol of amine.

6. The titration agent of claim 1, wherein the ratio of amine to sulfur dioxide is from 0.8:1 to 1.2:1.

7. The titration agent of claim 1, wherein the sulfur dioxide is in admixture with an acid in a molar ratio of sulfur dioxide to acid of 20:1 to 1:5.

8. The titration agent of claim 1, wherein the amine contains 1, 2 or 3 oxygen atoms.

9. A process for determining small quantities of water by the Karl Fischer method in which the titration agent employed is that claimed in claim 1.

10. The titration agent of claim 7, wherein the sulfur dioxide is in admixture with an acid selected from the group consisting of sulfuric, hydriodic and carboxylic acid in a molar ratio of sulfur dioxide to acid of 20:1 to 1:5.

11. The titration agent of claim 8 wherein the molar ratio of sulfur dioxide to acid is 2:1 to 1:2.

12. The titration agent of claim 10, wherein the acid is a carboxylic acid.

13. The titration agent of claim 12, where in the molar ratio of sulfur dioxide to carboxylic acid is 2:1 to 1:2.

14. The titration agent of claim 10, wherein the carboxylic acid is selected from the group consisting of formic, oxalic and acetic acid.

* * * * *